United States Patent [19]
Culoso

[11] Patent Number: 5,871,562
[45] Date of Patent: Feb. 16, 1999

[54] AIR CONDITIONING ODOR CONTROL APPARATUS AND METHOD

[76] Inventor: Richard Culoso, 6865 NW. 74th Ct., Parkland, Fla. 33067

[21] Appl. No.: 895,359

[22] Filed: Jul. 16, 1997

[51] Int. Cl.$^6$ .................................................. B01D 47/02
[52] U.S. Cl. .................................. 95/26; 95/256; 96/243; 96/245; 96/262; 96/265; 96/272; 96/329
[58] Field of Search .............................. 55/220, 225, 227, 55/229, 240, 244, 270, 271, 276, 277, 279; 95/26, 256; 339/454; 96/243, 245, 262, 265, 272, 329

[56] References Cited

U.S. PATENT DOCUMENTS

| | | | |
|---|---|---|---|
| 2,931,459 | 4/1960 | Wiles et al. | 55/227 |
| 3,142,548 | 7/1964 | Krantz | 55/227 |
| 3,389,971 | 6/1968 | Alligter | 55/244 |
| 3,442,603 | 5/1969 | Lazaros | 55/244 |
| 3,719,327 | 3/1973 | McMahan | 239/454 |
| 3,793,807 | 2/1974 | Prem Das | 55/244 |
| 4,005,999 | 2/1977 | Carlson | 55/244 |
| 4,121,915 | 10/1978 | Anderson | 55/227 |
| 4,448,593 | 5/1984 | Spiers | 55/227 |
| 4,731,224 | 3/1988 | Kawashima | 55/279 |
| 4,746,336 | 5/1988 | Mignot | 55/227 |
| 4,797,132 | 1/1989 | Vanvlack | 55/227 |
| 5,017,201 | 5/1991 | Park | 55/244 |

*Primary Examiner*—Jay H. Woo
*Assistant Examiner*—Minh-Chau T. Pham
*Attorney, Agent, or Firm*—Robert M. Downey, P.A.

[57] ABSTRACT

An apparatus and method for introducing a liquid substance into air flowing into an environment includes a main container for containing a reservoir of the liquid substance, and exhaust fan for withdrawing air from within said container to thereby create a negative air pressure condition therein, an air intake port having an upper open end exterior of the container and a lower open end within the container and in close adjacent relationship to a top surface of the reservoir of liquid, and a resupply container connected to the main container and including a pump to resupply liquid to the main container. Operation of the exhaust fan creates an air flow through the air intake port, causing the stream of air exiting the lower open end to impinge upon and agitate the top surface of the liquid, resulting in evaporation of the liquid into the air in the container. The mixture of droplets/vapor and air in the container are removed by the exhaust fan and introduced into a stream of air flowing into a selected environment.

12 Claims, 1 Drawing Sheet

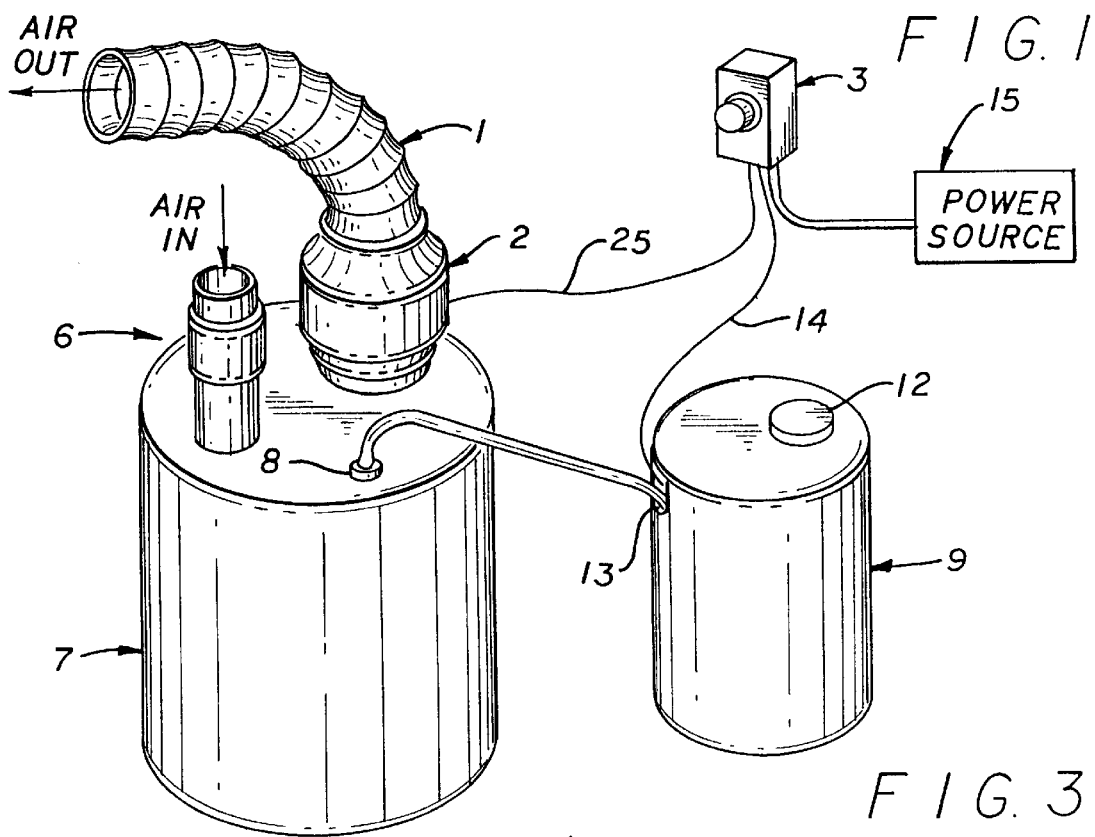
FIG. 1
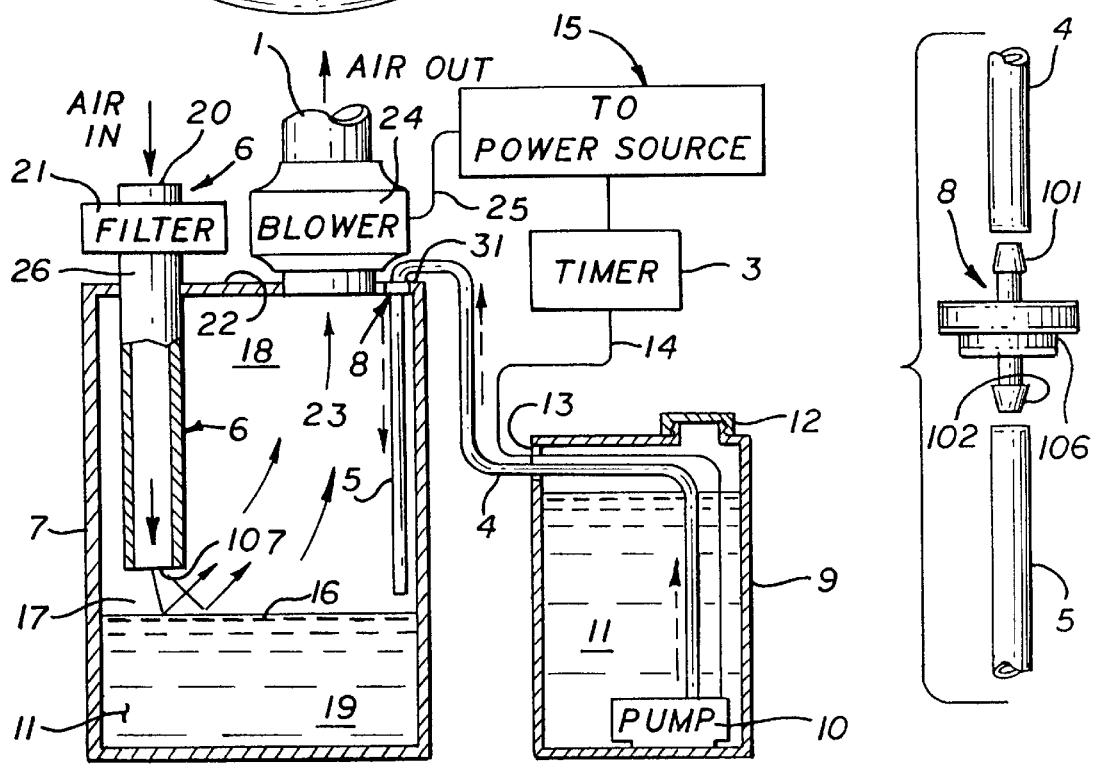
FIG. 2
FIG. 3

AIR CONDITIONING ODOR CONTROL APPARATUS AND METHOD

FIELD OF THE INVENTION

This invention relates to an apparatus and method for introducing an odor neutralizing substance, normally stored in liquid form, into air flowing into an environment which is generally closed, such as a closed store or room. The invention may be referred to as an odor control system or an odor sentry system.

BACKGROUND OF THE INVENTION

In numerous situations, there is a desire, indeed, often a need, to treat gas, particularly air, located in a somewhat confined area in order to remove, mask, and/or eliminate offensive odors. One example might be at a pet shop located in a strip or group of shops; another example might be in a particular location or locations within a hospital environment.

In the past, in view of these examples and numerous other situations, there has developed a crowded art directed toward solution for this long outstanding problem. Proposed solutions have ranged from technical, expensive and complicated apparatus and systems to the simplest of devices, such as a finger operated spray nozzle to release some masking odors from a container in a home; more simply, a wick with one end in a container of deodorant and a free end exposed to the air in the interior space of an automobile have been employed.

GENERAL DESCRIPTION OF THIS INVENTION AND ITS PURPOSE

This invention is of an improved apparatus and method useful to treat odorous air often encountered in confined locations. The apparatus is composed of easily assembled inexpensive items which can be relatively easily installed and operated. The apparatus and method are effective to treat air to neutralize offensive odors; and the apparatus and method are different and not obvious as a whole from the many prior apparatuses and methods of the prior art which address the problem.

DESCRIPTION OF THE PRIOR ART

Representative prior art is discussed generally in U.S. Pat. No. 5,261,933 relating to "A System for Deodorizing And/Or Treating Gas, Particularly A System for Deodorizing Gas Escaping From Plumbing Vents." Systems for prior art deodorizing and/or treating gas discussed in that patent are disclosed in U.S. Pat. Nos. 3,638,402; 1,383,938; 1,034,862; and 810,733. Also discussed in that patent is the fact that to treat odors in gasses, the gasses have been filtered through copper mesh or metal wool, see U.S. Pat. No. , 3,638,402. Further, gasses are treated by solid chemical material as disclosed in U.S. Pat. Nos. 1,383,938 and 810,733. Finally, in U.S. Pat. No. 1,034,482, it was taught to generate dry formaldehyde gas by vaporizing wood alcohol and the formaldehyde, the product of which is used to deodorize sewer gas.

SUMMARY OF THE PRESENT INVENTION

Generally, this invention is of portable components which can be easily assembled and installed as an operable apparatus for use in treating otherwise odorous or noxious air flow supplied to a somewhat confined area and which comprises means for substantially continually introducing a correct amount of treating liquid from a main container. The treating liquid from the main container is resupplied with replacement amounts of the treating liquid from a reservoir, which is included in and operably connected in the apparatus. This involves cyclically transferring and metering correct replacement amounts of treating fluid from a reservoir or storage container to the main apparatus container from which it is cyclically or continuously evaporated and introduced into the flow of air to the confined area. The invention also involves the disclosed method of treating the air supplied to the confined area.

BRIEF DESCRIPTION OF THE DRAWINGS

In accordance with the foregoing, the apparatus and method are described on reference to the attached drawings in which:

FIG. 1 is a pictorial representation of the apparatus in general form and illustrating the invention;

FIG. 2 is a view, partially in cross-section, of FIG. 1; and

FIG. 3 is an enlarged and exploded view of a pressure compensating drip nozzle 8, which is also seen at the left of the larger drum 7 seen in FIG. 2.

DETAILED DESCRIPTION OF THE PREFERRED EMBODIMENT

The air treatment apparatus is shown generally in FIG. 1. It is composed of liquid container means which, as illustrated, includes two tank portions: a first or main portion which may be in the form of a relatively large drum 7 and a second, supply or reservoir portion which may be in the form of a pail 9. The pail 9 is provided preferably with a charging port normally closed by cap 12. Adjacent the upper end of the pail 9 and in the side wall of it, a U-shaped notch 13 is provided for passage of an electrical conductor wire 14 and a tube or supply hose 4 for the purposes to be described more fully hereinafter.

The supply hose 4 constitutes liquid conductor means which interconnects the drum 7 and pail 9 of the liquid container means. Within each of these elements, the drum 7 and pail 9, of the container means, there is provided a supply of odor neutralizing liquid 11, preferably a liquid sold under the trademark "OdorMagic," which is an odor neutralizer product of HCI, the name of a business which is located at 6574 North State Road 7 in Coconut Creek, Fla. 33073. The preferred "OdorMagic" treatment liquid 11 is odorless yet effective to neutralize noxious odors in air into which it is introduced, although some users may prefer it have a faint trace of a selected odor such as a pine tree scent. Other types of treatment liquids appropriate for the use intended may also be utilized with the instant apparatus and method.

Means are provided to flow replacement amounts of treatment liquid from the supply or reservoir portion, i.e., the pail 9, to the main portion or drum 7. This might be done, for example, by a gravity and metered feed means, not shown. For example, the pail may be located above the drum to create a head and cause flow through a metering device to replace used amounts withdrawn from the drum 7 in use of the apparatus and method.

In the preferred embodiment shown, the means to flow replacement liquid preferably constitutes a pump 10 within the pail 9 which is connected electrically by the wire or electrical conductor 14 through a timer 3 to a power source generally indicated as at 15. Operation of the pump periodically or continually forces resupply liquid in container 9 to flow to tank 7 through metering device 8 and tube 5 extending downwardly in drum 7. The metering device 8 is also seen in FIG. 3 and is described more fully hereinafter.

The metering device 8 comprises a suitable means to meter a predetermined, limited replacement flow volume per given unit of time. As shown, this may be in the form of a pressure compensating drip nozzle indicated by the numeral 8, see FIG. 3 as well as FIG. 2. Such devices are commercially available and widely used in irrigation projects. The purpose of the metering means is to continually resupply liquid evaporated from the main tank in use of the method, the amount of the resupply being of substantially the same volume or amounts corresponding to that used. Hence, this constitutes means to maintain substantially the liquid level or surface 16 in the tank or drum 7 within a relatively narrow intermediate zone 17, that is between an upper zone 18 and a lower zone 19, of the drum 7. Thus, the liquid level or surface is at a generally constant level and in any event within a limited and tight range. The means to maintain a relatively constant liquid level in the drum 7 is significant in the use of the apparatus and method.

The drum 7 is provided with a gas intake port means generally indicated by the numeral 6, see FIGS. 1 and 2. The port means has a tubular portion 26 leading generally through the upper zone 18 of tank 7. Also, the tubular portion 26 has an exteriorly accessible upper opening 20. The tubular portion 26 preferably includes a filter means 21; and it also has a lower opening 107 opening to the intermediatezone of the tank 7 or main portion. Significantly, this opening 107 is closely adjacent the intermediate zone and at all times is little distance above the liquid surface 16.

In the lid 22 of the drum 7, there is provided an exhaust opening 23 through which air mixed with evaporated treatment liquid is withdrawn by a blower means or fan 2. The gas or air, which has been treated by its impinging flow on the liquid surface at the juncture of the intermediate zone 17 and lower zone 19 and subsequent swirling of it within the upper zone 18 of the drum 7, is a mixture of air and treatment material. It is discharged into a duct system 1 providing air flow to a generally closed area. Indeed, if desired, it may be introduced directly into a closed area instead of through an air duct.

Electrical circuit means are provided to interconnect the blower means or fan 2 to a power source, such as that indicated by the numeral 15. This circuit means portion is designated by the numeral 25. Also, a circuit means portion 14 interconnects the pump 10 and timer 3 to the power source 15, in the event this illustrated embodiment is employed. This is effective to intermittently operate the pump as required to deliver a resupply liquid flow to the pressure compensating drip nozzle 8, as shown in detail in FIG. 3; this nozzle will be described following the brief description of the use of the invention in the following paragraph.

In use, the drum 7 holds a supply of liquid odor neutralizing liquid; and the pail 9 holds a resupply of the liquid. A pump 10 in the pail 9 or container means portion periodically pumps a resupply amount of odor neutralizing liquid corresponding to the amount periodically used in operation of the method and apparatus through a hose 4 into the larger drum 7 through a supply hose 5 in the drum 7. The resupply is sufficient to correspond to and to replace that amount removed from drum 7. The pump 10 is controlled by a timer 3 which activates the pump for predetermined time intervals as required, for example, once every few hours up to 12 or 24 hours. The resupply is sufficient to maintain the liquid level substantially constant. The air intake tube with a filter 21, which extends down through the top of the larger drum 7, terminates at the open end 107 adjacent the surface of the liquid odor neutralizing substance 11 contained in the drum 7. The space between the opening 107 and the liquid surface 16 is thus maintained relatively constant, that is within a tight range. The centrifugal fan is preferably threadably connected to the top or lid 22 of the large drum 7. A flexible duct 1 may be provided. It connects to the output of the centrifugal duct fan 2 connecting the treated air output to either the air conditioning return plenum or directly to an air vent into a room or confined area. In short, the duct fan 2 draws air from within the drum 7 and forces it through the flexible duct 1 for delivery to the air conditioning system, or other air outlet, after air has been drawn through the top end of the air intake tube 6 to impinge upon the surface 16 of the liquid odor neutralizer substance 11 immediately after exiting the opening 107, all as indicated by the directional arrows in FIG. 2. The close impingement of the air flow on or about the liquid surface 16 causes agitation of the liquid, at the surface, and evaporation, as well as some concentration of fine droplets in the air flow leading to the fan.

In summary, if the fan means 2 operates continuously during a given time period, say for 12 or 24 hours, then the surface level of the liquid 16 would descend a slight level from the lower opening 107 of the inlet pipe 6. The timer for the pump will be set to replace the liquid which is used raising the level of the surface so that it remains relatively constant and close to the open end 107. Optimally, the liquid level 16 will remain at a constant level by simultaneous operation of the fan and means to maintain the liquid level. In a somewhat less efficient mode, the level 16 will be as shown in FIG. 2, that is at the lower level of the intermediate zone and the liquid which has been used is then replaced to raise the level 16 toward, but not to, the level of the open end 107. This structure which is employed to carry out this concept broadly is defined to be means to maintain the liquid level 16 substantially constant at the most efficient spacing of the end 107 above the liquid level 16, i.e., the location at which gurgling noise just ceases as the tube end 107 is withdrawn upwardly. The zone between a) the liquid level 16 and b) the open end 107 of tube 6 which is sufficient is defined as the intermediate zone.

In the preferred embodiment, the previously mentioned pressure compensating drip nozzle 8, see FIG. 3, is used to control or meter the rate at which the liquid is replenished in the larger drum 7 from the pail 9. Referring now to FIG. 3, the pressure compensating drip nozzle 8 is shown. It is a commercially available item which includes a nose portion 101 to connect to the end of the supply tube 4 as well as a foot 102 to connect to the hose 5. Between the portions 101 and 102, there is a pressure compensating drip nozzle means portion and a shoulder 106 which is connected in assembly about the opening 31 of the lid 22. This permits drip passage of replenishing liquid at a predetermined rate until a predetermined volume has passed therethrough over a give time period. Thus, in use, once the apparatus is installed, the amount of treatment liquid which evaporates in a given period of time from the drum 7 will be replaced. In this manner, from the reservoir pail 9, a resupply is provided to maintain the liquid level 16 in a tight range, that is at a relatively constant level. Once installed, there may be a periodic, weekly or monthly, resupply charged into the pail 7 of the system.

Generally, the system should be located relatively close to an air conditioner return and near a standard grounded electrical outlet or power source. The liquid, preferably OdorMagic, and water are introduced into the container means in a preferred concentration after being mixed well.

The centrifugal fan 2 upon being energized in a grounded outlet with a suitable switch may be energized. Of course, as is conventional, the pump is primed. This may be done by holding the end of a polyvinyl hose over the opening in the reservoir drum and operating the pump using a manual switch on a timer. This is shut off when all the air has been bled from it which usually requires about 15 seconds. The end of the polyvinyl hose 4 is then attached to the valve included in the pressure compensating drip nozzle 8, which is commercially available and of the type often used in irrigation systems, with the pressure compensating drip nozzle 8 being inserted into the lid 22 of the evaporation drum. When the centrifugal fan has been turned on and the air intake tube at its lower end 107 is positioned just above the liquid level 16.

Correct positioning of the lower end 107 is accomplished by a first step of gradual movement of it toward the liquid level 16 which causes a gurgling noise increasing intensity and, as a next step, a withdrawal characterized by a gradual loss of the gurgling noise until it is inaudible.

In a preferred embodiment, the duct is a 4" flexible type while the duct fan is conventional. Preferably, a conventional heavy duty 24 hour timer 3 is utilized and, also, the polyvinyl or polyethylene supply hoses are of ¼" OD. A 2" polyvinyl chloride air intake tube is provided as at 26 and preferably a commercially available filter cap indicated by the numeral 21 is provided. In use, it has been found that a 20-gallon evaporation drum constitutes a satisfactory embodiment while a 12-gallon reserve pail is suitable for four week renewal cycles. The pump 10 is of the submersible type, ¹⁄₁₀₀ to ¹⁄₁₅₀ horsepower is inadequate. Finally, it is recommended that the evaporization drum 7 and the reservoir or pail 9 be emptied and sanitized twice a year or generally at six month intervals.

While this invention and method of using the apparatus described are illustrated in a preferred embodiment, it is recognized that departures can be made as indicated in the written materials contained herein or within the scope of the knowledge of those skilled in the art; and, therefore, the overall combination of the apparatus and method should not be limited except by the claims and the doctrine of equivalents to accord the full scope of protection.

What is claimed is:

1. An apparatus adapted for connection to a power source for introducing a liquid substance into an air space exterior of the apparatus, said apparatus including:
    liquid container means for containing the liquid substance therein, said liquid container means comprising:
        a main portion having an upper zone, a lower zone, and an intermediate zone, and
        a separate resupply portion, said resupply portion including a normally closed charging port;
    conduit means interconnecting the main portion and the resupply portion for transferring therethrough a replenishing supply of the liquid substance from the resupply portion to the main portion;
    means for flowing liquid from the resupply portion to the main portion through the conduit means;
    means to maintain a top surface of the liquid substance in the container means at a generally constant level within the intermediate zone at all times during use of the apparatus;
    air intake means in the upper zone of the main portion and including a tubular portion having an upper inlet opening exterior of the container means and a lower outlet opening within the upper zone of the main portion and closely adjacent the intermediate zone;
    air outlet means in the main portion communicating with the upper zone and an exterior of the main portion of the liquid container means; and
    blower means for removing air from the upper zone of the main portion of the liquid container means through said air outlet means so as to create a negative pressure condition therein and to thereby cause air to be drawn through said upper inlet opening of said tubular portion so that the air exits the lower outlet opening and impinges upon the top surface of the liquid substance, resulting in agitation and evaporation of the liquid substance and mixture of small droplets and vapors of the liquid substance with air in the upper zone for subsequent removal through the air outlet means.

2. The apparatus as recited in claim 1 wherein the means to maintain comprises pump and metering means and associated timer means to force liquid from the resupply portion to the main portion through said conduit means and to maintain a relatively constant treatment liquid level in the main portion while in use.

3. The apparatus as recited in claim 1 wherein the intermediate zone is spaced from the liquid level a distance such that all gurgling noise has just disappeared from the impinging flow on the liquid level.

4. The apparatus as recited in claim 1 wherein the main portion comprises a drum and the resupply portion comprises a pail.

5. The apparatus as recited in claim 4 wherein the means for flowing comprises a pump in said pail.

6. The apparatus as recited in claim 1 wherein the means to maintain a liquid surface of a treatment liquid at a generally constant level within the intermediate zone at all times in use comprises a metering means in the conduit means.

7. The apparatus as recited in claim 6 wherein said metering means comprises a pressure compensating drip nozzle means to permit flow of treatment liquid from the resupply portion to the main portion in a volume which corresponds to the volume of mixed treatment liquid droplets and vapors removed from the main portion maintaining the liquid level in the main portion generally constant at all times in use.

8. The apparatus as recited in claim 1 wherein said air intake means includes filter means to filter air flow through the intake port means.

9. The apparatus as recited in claim 1 wherein said blower means are operatively connected to said main portion of said container means.

10. A method of introducing a liquid substance into an air space comprising the steps of:
    removing air from an upper portion of a main container having a reservoir of the liquid substance contained in a lower portion thereof;
    creating a negative air pressure condition within said main container;
    causing a stream of air flow to enter through a first open end of an air intake on said main container;
    directing the stream of air flow through the air intake and out from a second open end of the air intake and into said main container;
    maintaining a level of a top surface of the liquid substance substantially constant at an intermediate portion of the main chamber, between the lower portion and the upper portion;
    maintaining the second open end of the air intake closely adjacent the top surface of the liquid substance in the main container;

causing the stream of air flow to impinge upon the top surface of the liquid substance and agitating the liquid substance at the top surface to cause droplets of the liquid substance to enter the air in the upper portion of the main container and thereby creating a mixture of air and vapor containing the liquid substance;

removing the mixture from the upper portion of the main container; and feeding the mixture into a stream of air flowing to the air space so that the droplets of the liquid substance become dispersed in the air space.

11. The method as recited in claim 10 wherein said step of maintaining the level of the top surface of the liquid substance in the main container substantially constant comprises the step of continually resupplying the liquid substance into the lower portion of the main container from a separate supply reservoir of the liquid substance.

12. The method as recited in claim 11 further comprising the step of:

initially adjusting the second open end of the air intake relative to the top surface of the liquid substance including first advancing the second open end toward the top surface of the liquid substance in the main container to cause a substantially gurgling sound as the stream of air flow impinges upon the top surface of the liquid substance and thereafter withdrawing the second open end until the gurgling noise just terminates.

* * * * *